United States Patent [19]

Sustmann

[11] Patent Number: 4,699,618
[45] Date of Patent: Oct. 13, 1987

[54] FLUFF FREE TAMPON AND METHOD FOR MAKING

[75] Inventor: Scarlet Sustmann, Viersen, Fed. Rep. of Germany

[73] Assignee: Vereinigte Papierwerke, Schickedanz & Co., Nuermberg, Fed. Rep. of Germany

[21] Appl. No.: 606,079

[22] Filed: May 1, 1984

[30] Foreign Application Priority Data

May 5, 1983 [DE] Fed. Rep. of Germany ....... 3316431

[51] Int. Cl.$^4$ .............................................. A61F 13/16
[52] U.S. Cl. .................................... 604/365; 604/370; 604/904
[58] Field of Search ................ 604/285, 286, 365–367, 604/369, 370, 380, 382, 904

[56] References Cited

U.S. PATENT DOCUMENTS

| 3,545,442 | 12/1970 | Wicker | 604/370 |
| 3,855,046 | 12/1974 | Hansen et al. | 604/366 |
| 3,976,075 | 8/1976 | Chinai et al. | 604/365 |
| 4,054,141 | 10/1977 | Schwaiger et al. | 604/366 |
| 4,275,105 | 6/1981 | Boyd et al. | 604/370 |
| 4,333,979 | 6/1982 | Sciaraffa et al. | 604/366 |
| 4,543,098 | 9/1985 | Wolfe et al. | 604/904 |

FOREIGN PATENT DOCUMENTS 3236540 9/1982 Fed. Rep. of Germany.
3236541 9/1982 Fed. Rep. of Germany.

Primary Examiner—John D. Yasko
Attorney, Agent, or Firm—Ernest G. Szoke; Henry E. Millson, Jr.

[57] ABSTRACT

To wrap a hygienic fleece consisting of a cotton wool web in fluff-proof form without the need for a separate nonwoven material, synthetic fiber is added to the starting material in a quantity sufficient for thermoplastic consolidation of the surface and a surface of the prepared cotton wool web is consolidated to give a nonwoven finish. A calender comprising at least one heating embossing roller is used.

10 Claims, 2 Drawing Figures

FLUFF FREE TAMPON AND METHOD FOR MAKING

BACKGROUND OF THE INVENTION

1. Field of the Invention

This invention relates to a hygienic fleece consisting of a web of cotton wool covered by a fluff-proof nonwoven surface layer. It also relates to a method of making this fleece.

2. Description of the Prior Art

Web-form cotton wool fleeces are widely used for absorbing body fluid, for example, in surgical dressings, panty liners and in plugs of the type used for absorbing menstrual secretion (so-called tampons). In the manufacturing process, the cotton wool web is consolidated either by calendering or by needle punching and subsequently compressed into cylindrical form. Since the starting material consists of individual fibers having an average length of from 20 to 40 mm, fibers or pieces of cotton wool can remain behind in the wound, vagina, etc. after removal of the surgical dressing or tampon and can cause inflammation.

Accordingly, attempts have been made to prevent the release of fluff by separately wrapping the cotton wool web in a nonwoven material. In such processes, a cotton wool web is wrapped overlappingly in a nonwoven fabric or the like. In the manufacture of tampons, the cotton wool web is then cut into lengths and, after the recovery cord has been attached, is introduced into a compression chamber either linearly or after turning through 90°. The tampons obtained in this way are either fully wrapped longitudinally and open at either end or, alternatively, are wrapped at their ends and have an open cut surface extending in the longitudinal direction.

Processes for completely wrapping a tampon are described in German application Nos. 32 36 540 and 32 36 541. In the first application, No. 32 36 540, complete wrapping of the tampon is obtained by a process in which the free cut edges formed after wrapping of the cotton wool web in a fluff-free material are folded over onto the surface of the wrapped cotton wool web and pressed onto that surface. To that end, the manufacturing process comprises a corresponding step in which the length of cotton wool web separated off and wrapped passes onto a guide belt where it is folded over by means of guide plates at the free cut edges and subjected to compression.

In the process according to the second application, No. 32 36 541, the edges remaining open after wrapping of the cotton wool web in the covering material and separation into individual lengths are sealed.

In all processes other than that described and claimed herein, a separate nonwoven material is required for wrapping the cotton wool web. This requirement is unfavorable both in regard to the consumption of material and also in regard to the manufacturing equipment and procedures involved.

DESCRIPTION OF THE INVENTION

Figure 1:
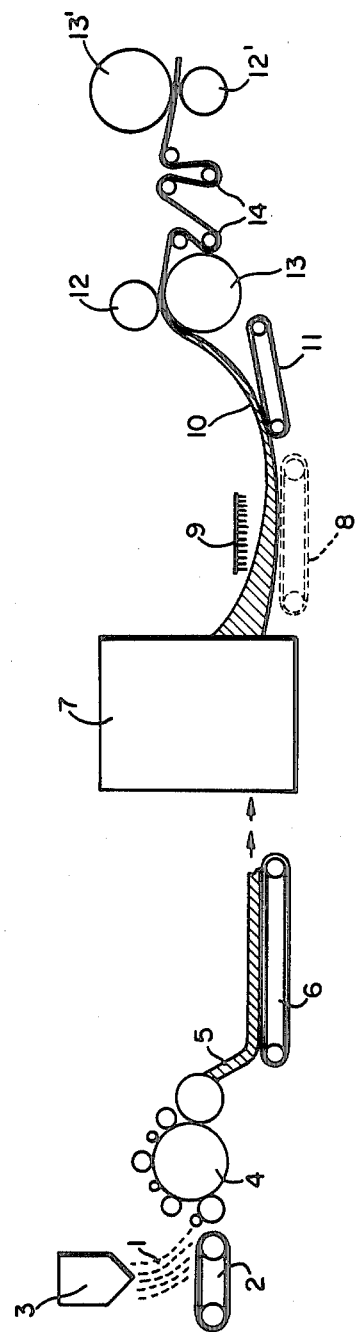
FIG. 1 shows the production of a cotton wool web having a fluff-proof surface layer.

The object of the present invention is to provide a hygienic fleece which is inexpensive to produce, does not form any fluff and which, despite its excellent absorbency, does not require a separate non-woven wrapping. According to the invention, this object is achieved in a hygienic fleece by a hot-embossed surface consolidation of a thermoplastic or meltable fiber component of the cotton wool web to form an embossed, nonwoven, fluff-proof surface layer.

The present invention also relates to a method for making a hygienic fleece comprising a cotton wool web covered by a fluff-proof nonwoven surface layer, wherein a cotton wool web is prepared with a synthetic fiber component amenable to thermoplastic consolidation (herein, sometimes referred to as a "thermoplastic fiber") of the surface and in that at least one surface of the prepared cotton wool web is continuously or intermittent consolidated in the form of a nonwoven layer in a calender comprising at least one working roller with a heated embossing surface.

The fact that, before entering the tampon machine or the like which forms the appropriate lengths, the prepared cotton wool web passes through a heated calender resulting in the "in situ" formation of a nonwoven surface layer on the cotton wool web thus treated, during which the surface layer remains part of the cotton wool web and is joined firmly thereto. Depending on the application envisaged, it is also possible in this way to convert both surfaces of the cotton wool web into fluff-proof coverings. Finally, all the edges, including the cut edges, also called divided edges or parting lines, and side edges (also called longitudinal edges) of the web can also be sealed in fluff-proof form by the heat sealing process of the invention.

The calender used to form a fluff-proof surface on the upper surface and/or underneath of the cotton wool web should preferably comprise one or two pairs of rollers. A heated embossing roller, for example having a rhombic or hexagonal pattern, and a counter roller belong to each pair of rollers.

The temperature of the heated embossing rollers or working rollers is adjusted to suit the thermoplastic fibers used and of course, takes into account the melting temperature of a particular thermoplastic fiber used. Where polypropylene fibers are used in a proportion of 20%, embossing temperatures in the range of from about 150° to about 160° are suitable.

The pressure applied by the calender is best increased when the cotton wool web passes through at relatively high speeds and decreased when the web passes through at lower speeds. In other words, the calender pressure and the throughput rate are selected to be substantially inversely proportional. The calender pressure can be in the range of from about 0.5 to about 2 bars. The patterning of the embossing or working rollers is also selected in accordance with the material to be treated. The reliefs can have a diameter of, for example, from about 0.5 to about 3 mm.

A cotton wool web for tampons can be produced, for example, from a mixture of standard tampon material, for example, 100% rayon staple fiber, preferably with a denier of 2.8 to 3.6 dtex and a fiber length of 30 to 40 mm, and approximately 20% of a thermoplastic fiber. Representative standard tampon materials include rayon, cotton or mixtures hereof.

Representative suitable thermoplastic fibers include polypropylene, polypropylene/polyethylene (for example Chisso ES bicomponent fiber), polyester, Heterofil-fibers (ICI).

The fibers can be mixed in a weighing box feeder. The thermoplastic fiber is used in an amount of from 5 to 20% of the total fiber content of the cotton wool web, more preferably from 10 to 20% and most preferably about 20%, if no fiber seperation is made. In effecting fiber seperation in an air laying process—as for example in a K 12/74 air laying unit of Fehrer, the thermoplastic fiber may be favourably present in amounts as low as about 5%. Further processing is then carried out by carding, followed by calendering to form a cotton wool web having the required width, for example from about 50 to about 90 mm.

Instead of being produced by carding, the cotton wool web can also be produced by needle punching. It is pointed out at this juncture that, in the manufacture of tampons, it is important in carrying out the present invention for the cotton wool web to pass through the heated calender containing at least one embossing roller before entering the tampon machine which divides the cotton wool web into suitable lengths and compresses those lengths to form finished tampons. In producing rolled tampons only one surface of the cotton wool band is consolidated in the form of a nonwoven layer, preferably in an intermittent way, so that fluff-proof segments result which form the surface of the tampon. This is effected by a suitable calander with protruding heated embossing segments and interstices where no bonding takes place. In this case the calander before the tampon machine can be replaced by a well timed heated embossing die.

The roller embossing according to the invention with embossed lines, points, or lines and points also has an important bearing on the softness of the surface. By contrast, whole-surface solidification would result in relatively stiff lengths of the cotton wool web which would not be easy to compress. Absorbency is also improved by "spot" solidification.

The edges, including end edges and side edges, of the individual lengths of cotton wool web can also be solidified, particularly by heat sealing. However, cut edges which have not been sealed in this way may, of course, also be displaced into the interior of the tampon or the like by special folding techniques of the type described in the German Patent Applications referred to earlier.

In addition to tampons, panty liners, wound dressings and the like can also be produced by the process of the invention. Instead of wrapping a cotton wool web in a separate nonwoven material, a cotton wool web surface consolidated on one or both sides and thus, as it were, closely bound up with a nonwoven material, is produced by the hot embossing system of the invention.

For example, in the production of panty liners, webs of the nonwoven material of the invention, weighing from about 110 to about 200 g/m² are prepared, folded into a U, and covered on one side with liquid-impermeable underwear protection, for example, a polymeric material impermeable to liquids, such as a polypropylene (PP) or polyethylene (PE) film. The ends are formed by a standard embossing/stamping process.

Liners can also be produced from a web-form or sheet form material by a sealing-embossing/stamping process. In cases where several predetermined embossing patterns are applied to a single rotating embossing roller, it is also possible economically to produce a corresponding number of liners at the same time.

Embodiments of the invention are described by way of the following examples, which make reference to the accompanying drawings, wherein:

FIG. 1 shows the production of a cotton wool web having a fluff-proof surface layer.

Figure 2:
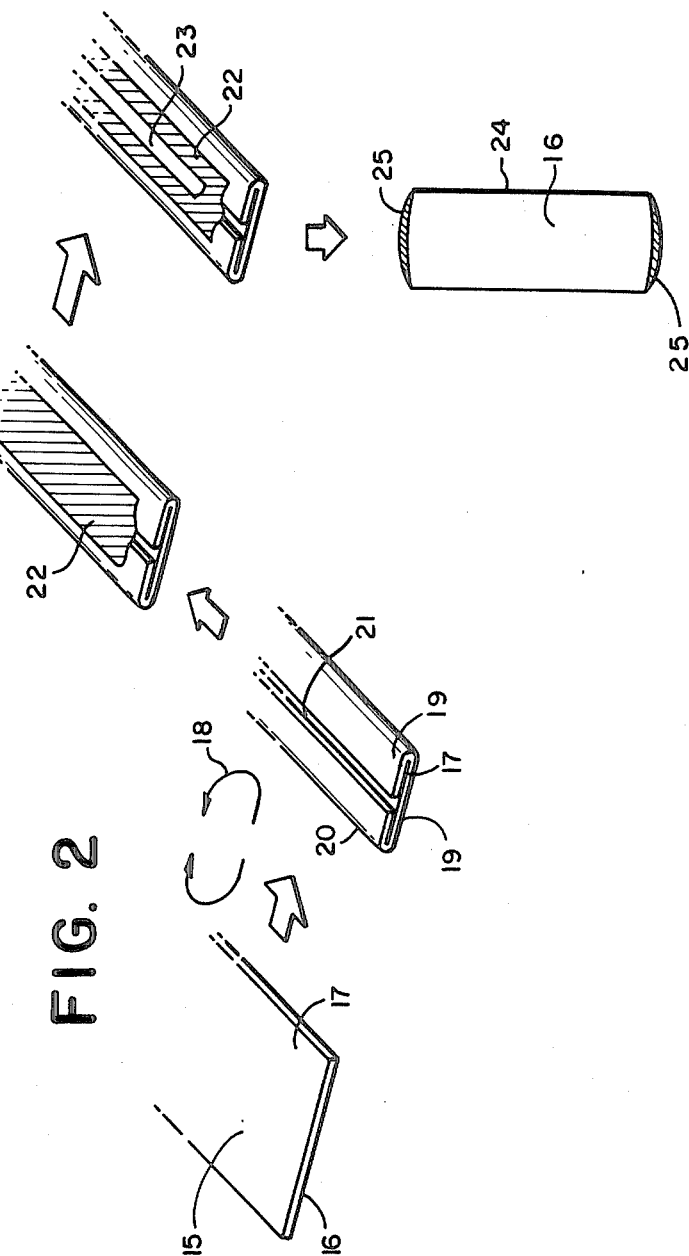
FIG. 2 shows the procedure involved in the production of panty liners.

FIG. 2 shows the various stages involved in the production of panty liners.

Although the examples illustrate the invention as claimed, they are not to be construed as limitations thereon.

EXAMPLE I

Production of tampons

1. Production of the cotton wool web

A fiber mixture of 80% rayon staple fiber (denier 3.6 dtex, fiber length 30 mm) and 20% polypropylene fibers (denier 3.0 dtex, 1⅞", matt) was produced by a standard loosening technique, more particularly by carding, and made up into a cotton wool web weighing 728 g/m² which was then consolidated by needle punching.

As shown in FIG. 1, a rayon staple/polypropylene mixture 1 was transported by a conveyor belt 2 from a weighing box feeder 3 onto a card 4 comprising workers and strippers. The resulting fibrous web 5 was transported by conveyor belt 6 through a preparing unit 7, in which it was converted into a random-fiber web, and finally onto a sieve belt 8 where it was treated by a needle puncher 9. The needle-punched (or, alternatively, calendered) cotton wool web 10 was then transported by another conveyor belt 11 into a heatable calender consisting of a heated steel engraving roller 12 and a cotton or plastic roller 13.

Tests have shown that a calender consisting of a heated steel engraving roller with fine cross-hatching and an oppositely mounted cotton roller is particularly favorable. Where the above materials were used, the temperature employed was 158° C. and the pressure was 0.5 bar for a throughput rate of 3 meters per minute. Soft, continuous surface consolidation was obtained on the cotton wool web 10.

The cotton wool web can be surface-consolidated to give a fluff-proof finish on both sides if another calender comprising another counter roller 13' acting on the already consolidated surface of the cotton wool web 10 and a steel engraving roller 12' acting on the unconsolidated surface of the cotton wool web is arranged after the first calender, optionally with guide rollers 14 in between. In this embodiment, the surface-consolidated part of the cotton wool web weighed approximately 15 to 20 g/m². It did not give off any fluff.

2. Tampon production (not shown in drawings)

The surface consolidated cotton wool web prepared as described above, was then cut up into lengths measuring 40×70 mm. At the same time, the cut edges, also called divided edges, were also consolidated, partly by means of a cutting and sealing machine. A recovery cord was then sewn onto each of the lengths of cotton wool web longitudinally thereof. The individual lengths were then axially and radially compressed by standard techniques to form cylindrical bodies and inserted into insertion tubes. The temperature applied during compression was in the range of from 100° to 120° C.

3. Performance testing

The tampons produced from the surface-consolidated cotton wool web were compared with tampons produced from the same fiber mixture, but without surface consolidation and with conventional tampons consisting entirely of rayon staple (3.6 dtex, 30 mm).

All three types of tampons were produced by exactly the same process given above except for the surface consolidation treatment. The tampons were tested for their geometry and absorbency after withdrawal from their insertion tubes. The results are shown in the Table located at the end of the specification. In the Table, the first line (1.) relates to a tampon produced from a surface-consolidated cotton wool web prepared as above in accordance with the invention. The second line (2.) relates to a tampon prepared as above, but without surface consolidation. The third line (3.) relates to a tampon consisting entirely of rayon staple, 3.6 dtex, 30 mm prepared as above but without surface consolidation.

Absorption capacity was determined by means of an artificial test vagina known as a Syngina. The test liquid used was water under an initial pressure of 30 mbar. The test was not conducted under isobaric pressure conditions; instead the pressure increased with increasing swelling through the absorption of liquid. In the Table, V represents the volume and G the density of the tampon. For the same weight per unit area of the constituent material, a tampon produced in accordance with the invention has a slightly smaller volume than a tampon produced without any surface consolidation, so that its density is slightly greater. However, absorbency with pressure increase is better in the tampon produced in accordance with the invention than in the other two tampons.

4. Results

The tampons containing 20% polypropylene expand on withdrawal from the tube and occupy a greater volume V than tampons of pure rayon staple. This may be regarded as an advantage because the tampons which are flexible and relatively soft after expansion conform closely to the walls of the vagina and effectively prevent liquid from penetrating past. By contrast, the tampons consisting entirely of rayon staple initially retain their rigid, rodlet shape and only begin to swell after contact with liquid.

Formation of the nonwoven surface layer does not affect absorption capacity. By comparison with tampons consisting entirely of rayon staple, the absorption capacity of the tampons containing polypropylene is increased by approximately 18%. This is attributable, inter alia, to the greater recovery power of that fiber mixture so that liquid can be taken up more quickly. Naturally, absorbency is also increased in this region in inverse proportion to density. The increase in pressure on contact with liquid is distinctly lower in the case of tampons containing polypropylene.

In overall terms, the tampons of 20% polypropylene and 80% rayon staple having the nonwoven surface layer formed in accordance with the invention are better than tampons consisting entirely of rayon staple for the following reasons:

(a) no release of fluff
(b) greater absorbency
(c) better lateral fit in the vagina
(d) reduced pressure formation, if any, under wearing conditions.

EXAMPLE II

Panty liners

Panty liners are produced using a standard panty liner machine of the type commonly used for producing the cotton wool-based liners. A cotton wool web weighing approximately 130 g/m$^2$ consolidated in the same way as in EXAMPLE I was cut into 100 mm wide strips 15 as shown in FIG. 2. The cotton strip 15 had a surface 16 provided with a fluff-proof finish in accordance with the process of the invention decribed in EXAMPLE I using one pair of rollers. Cotton strip 15 also has an open surface 17.

The cotton wool strip 15 was then folded on both sides in a manner shown by curved arrows 18, so that the consolidated surface 16 of the cotton wool strip forms the outside surface 19 of folded cotton wool strip 20, and forms a fold line 21. A moisture-impermeable film 22 was then bonded to the fold over fold line 21 as shown. The film 22 serves as underwear protection. An adhesive strip 23 was next applied, more particularly using a siliconized paper, to the film 22 in the usual way for fastening to underwear. Finally, the longitudinal ends 24 were finished, more particularly rounded off, and consolidated by means of a heated embossing roller (not shown), so that fluff-proof ends 25 are obtained. Embossing and consolidation are possible in that region because the cotton wool web contains thermoplastic fibers.

The process of the invention is particularly economical because there is no need for separate wrapping in a nonwoven material, eliminating all the problems which this normally involves.

TABLE

| | Weight of cotton wool (g) | Tampon length (mm) | Diameter (mm) | V (cc) | G (g/cc) | Absorption capacity, pressure increasing. | | Syngina 30 mbar test liquid: H$_2$O pressure increase |
|---|---|---|---|---|---|---|---|---|
| | | | | | | ml/tampon | ml/g | |
| 1. | 2.75 | 48.2 | 15.4 | 8.96 | 0.307 | 10.75 | 3.91 | 5.0 |
| 2. | 2.75 | 52.1 | 15.1 | 9.36 | 0.294 | 10.2 | 3.70 | 2.2 |
| 3. | 2.75 | 46.7 | 12.7 | 5.95 | 0.462 | 9.1 | 3.31 | 6.8 |

What is claimed is:

1. A fluff-proof tampon consisting essentially of an admixture of an absorbent fiber and a minor proportion of a thermoplastic fiber compressed into a cylindrical tampon body, and an attached recovery cord, wherein the tampon body is characterized by a hot-embossed substantially fluff-proof surface finish comprising thermoplastic fibers heat-consolidated with absorbent fibers.

2. In a tampon of the type wherein an absorbent fiber is formed into a cylindrical tampon body, the improvement comprising admixing the absorbent fiber before forming with a minor proportion of a thermoplastic fiber, compressing the admixture to form a compressed body, and hot-embossing the compressed body to heat-consolidate surface thermoplastic fibers with absorbent fibers and provide a substantially fluff-proof embossed surface finish on said tampon body.

3. The tampon of claim 1, wherein the surface thermoplastic fibers are only partially heat-consolidated.

4. The tampon of claim 2, wherein the surface thermoplastic fibers are only partially heat-consolidated.

5. The tampon of claim 1, wherein the absorbent fiber is rayon or cotton.

6. The tampon of claim 1, wherein the thermoplastic fiber is polypropylene or polyester.

7. The tampon of claim 6, wherein the thermoplastic fiber is polypropylene.

8. The tampon of claim 1, wherein the surface finish has a rhombic or hexagonal embossed pattern.

9. The tampon of claim 2, wherein the compressed body is a cotton wool web which is cut to length and formed into the tampon body after hot-embossing thereof.

10. The tampon of claim 9, wherein the length of hot-embossed and cut web is formed into the tampon body by rolling.

* * * * *